United States Patent
Park et al.

(10) Patent No.: US 9,241,621 B2
(45) Date of Patent: Jan. 26, 2016

(54) METHOD FOR CONTROLLING OPHTHALMIC DEVICE

(71) Applicant: MEDIZS Inc., Daejeon-si (KR)

(72) Inventors: Ji Hyoung Park, Daejeon-si (KR); Yu Kyeom Kim, Daejeon-si (KR); Ki Dong Lee, Daejeon-si (KR); Sung Yun Jin, Daejeon-si (KR); Bo Ra Kim, Daejeon-si (KR)

(73) Assignee: MEDIZS INC., Daejeon-Si (KR)

( * ) Notice: Subject to any disclaimer, the term of this patent is extended or adjusted under 35 U.S.C. 154(b) by 155 days.

(21) Appl. No.: 14/162,407

(22) Filed: Jan. 23, 2014

(65) Prior Publication Data

US 2015/0150446 A1 Jun. 4, 2015

(30) Foreign Application Priority Data

Dec. 3, 2013 (KR) .......................... 10-2013-0149465

(51) Int. Cl.
*A61B 3/02* (2006.01)
*A61B 3/028* (2006.01)
*A61B 3/00* (2006.01)

(52) U.S. Cl.
CPC ............. *A61B 3/0285* (2013.01); *A61B 3/0033* (2013.01)

(58) Field of Classification Search
CPC .. A61B 3/0016; A61B 3/0033; A61B 3/0041; A61B 3/0058; A61B 3/0066; A61B 3/0285; A61B 3/032; A61B 3/04; A61B 3/103; A61B 3/11; A61B 3/18; A61B 3/185

USPC ......... 351/204, 205, 222, 225, 227, 233, 237, 351/239
See application file for complete search history.

(56) References Cited

U.S. PATENT DOCUMENTS

| | | | |
|---|---|---|---|
| 8,167,429 B1 | 5/2012 | Butler et al. | |
| 2003/0081175 A1* | 5/2003 | Hosoi et al. | A61B 3/04 351/222 |
| 2007/0236665 A1* | 10/2007 | Sakurada | A61B 3/032 251/222 |

FOREIGN PATENT DOCUMENTS

KR 10-2011-0105491 9/2011

OTHER PUBLICATIONS

Application Form for attending MIDO 2013 in Milano, Italy, JH. Park of MEDIZS Inc., Nov. 14, 2012.
A printout of website regarding MIDO 2013 by MEDIZS Inc., pp. 1-4, Facebook, Mar. 2-4, 2013.

* cited by examiner

*Primary Examiner* — Huy K Mai
(74) *Attorney, Agent, or Firm* — Kile Park Reed & Houtteman PLLC

(57) ABSTRACT

A method for wireless control of an auto chart instrument and an auto phoropter by using a smart pad, comprising: control data inputting step for being inputted with control data for wireless control of one of the auto chart instrument and the auto phoropter; and controlling step for controlling one of the auto chart instrument and the auto phoropter according to the control data inputted during the control data inputting step, is disclosed.

20 Claims, 5 Drawing Sheets

METHOD FOR CONTROLLING OPHTHALMIC DEVICE

FIELD OF THE INVENTION

The present invention related to an ophthalmic instrument system, and more particularly to method for controlling ophthalmic instrument for eye examination.

DESCRIPTION OF THE RELATED ART

A phoropter (US trademark of Reichert Technologies)) is an instrument commonly used by eye care professionals during an eye examination, containing different lenses used for refraction of the eye during sight testing, to measure an individual's refractive error and determine his or her eyeglass prescription.

The phoropter includes a plurality of lenses such as spherical lenses, cylinder lenses, etc. which are combined for eye examination.

In addition, the phoropter performs eye tests such as eyesight test and color blindness test together with another ophthalmic instrument, a chart projector.

As a phoropter there are two types, a manual phoropter manually operated by rotating dials, and auto phoropter (digital refractor) automatically controlled by an operation panel.

But the whole cost for the digital refractor is high because the operation panel is necessary for the control of the digital refractor. Furthermore it is difficult to use an auto chart instrument of the other maker due to the compatibleness problem between the operation panel.

In addition, since the measurement data measured by the respective ophthalmic instruments cannot be transferred therebetween, the measurement data may be given by the display or the printed paper and cannot be saved, which makes integrated management and post management for the measurement data difficult.

SUMMARY OF THE INVENTION

Therefore, an object of the present invention is to provide a method for wireless control of ophthalmic instrument capable of easy operation and control by using a conventional smart pad in controlling ophthalmic instrument such as auto phoropter, auto chart instrument, etc.

Another object of the present invention is to provide a method for wireless control of ophthalmic instrument capable of integrated management and post management for the examination result of the ophthalmic instruments in which the ophthalmic instruments are controlled by receiving examination result from an auto Refractometer/Keratometer and an auto phoropter, saving the received examination data, and using the previously saved examination data in controlling the ophthalmic instruments.

To achieve these and other advantages and in accordance with the purpose of the present invention, as embodied and broadly described herein, there is provided a method for wireless control of an auto chart instrument and an auto phoropter by using a smart pad, which includes control data inputting step for being inputted with control data for wireless control of one of the auto chart instrument and the auto phoropter; and controlling step for controlling one of the auto chart instrument and the auto phoropter according to the control data inputted during the control data inputting step.

In the control data inputting step and the ophthalmic instrument controlling step, an image of a phoropter and control data for the auto phoropter may be displayed in a screen of the smart pad.

A portion of the image of a phoropter corresponding to a member of the auto phoropter to be controlled may be used as a control portion in the control data inputting step and the ophthalmic instrument controlling step.

The control data inputting step may include chart control portion displaying step for displaying chart instrument control portion in the main page, when the chart instrument control portion selected by user's touch; and chart control data receiving step for displaying at least part of a plurality of images in order to be inputted with chart control data for controlling the auto chart instrument in a state that the chart instrument control portion is removed or maintained when the chart instrument control portion is selected by user's touch.

The control data inputting step may include selected image displaying step for displaying the chart control data inputted in the chart control data receiving step after the chart control data receiving step.

The control data inputting step may include phoropter control portion displaying step for displaying phoropter control portion in a main page in order to be inputted with control data for at least one of spherical lenses, cylinder lenses, prism, polarizing lenses, cross cylinder lenses and a plurality of filters by user's touch; and control data displaying step for being inputted with control data for at least one of spherical lenses, cylinder lenses, prism, polarizing lenses, cross cylinder lenses and a plurality of filters by user's touch and displaying the control data in the main page.

After the control data displaying step, the finger number and the finger movement of user's finger touch to the screen of the smart pad may be recognized and control data for at least one of spherical lenses, cylinder lenses, prism, polarizing lenses, cross cylinder lenses and a plurality of filters is inputted by the finger number and the movement of user's finger touch.

The smart pad may be saved with a main page for displaying an image of a phoropter and control data for the auto phoropter; a chart control page for displaying at least part of a plurality of images for controlling the auto chart instrument in order to be inputted with control data for the auto chart instrument by user's touch; a phoropter control page for displaying at least one control portion in the image of a phoropter corresponding to a member of the auto phoropter to be controlled, the member being one of spherical lenses, cylinder lenses, prism, polarizing lenses, cross cylinder lenses and a plurality of filters in order to be inputted with control data for at least one of spherical lenses, cylinder lenses, prism, polarizing lenses, cross cylinder lenses and a plurality of filters by user's touch; and a data displaying page for displaying examination data received from an auto Refractometer/Keratometer and phoropter data showing status of the auto phoropter, wherein the respective pages are respectively displayed in the whole screen of the smart pad when displayed in the screen of the smart pad, and the main page, the chart control page, the phoropter control page, and the data displaying page are changed among others by at least one of user's touch and button control of the smart pad.

The control data may be inputted by at least one of user's finger operation and a pen in the control data inputting step.

The finger number and the finger movement of user's finger touch to the screen of the smart pad are recognized and the control data is inputted by the finger number and the movement of user's finger touch in the control data inputting step.

The method may further include examination data receiving step for receiving examination data from an auto Refractometer/Keratometer by wireless communication.

The examination data received from an auto Refractometer/Keratometer in the examination data receiving step may be used for being inputted with the control data for wireless control of at least one of the auto chart instrument and the auto phoropter in the control data inputting step.

According to another embodiment, there is provided a method for wireless control of an auto chart instrument and an auto phoropter by using a smart pad, comprising: control data inputting step for being inputted with control data for wireless control of one of the auto chart instrument and the auto phoropter; and controlling step for controlling one of the auto chart instrument and the auto phoropter according to the control data inputted during the control data inputting step, wherein the smart pad is saved with: a main page for displaying an image of a phoropter and control data for the auto phoropter; a chart control page for displaying at least part of a plurality of images for controlling the auto chart instrument in order to be inputted with control data for the auto chart instrument by user's touch; a phoropter control page for displaying at least one control portion in the image of a phoropter corresponding to a member of the auto phoropter to be controlled, the member being one of spherical lenses, cylinder lenses, prism, polarizing lenses, cross cylinder lenses and a plurality of filters in order to be inputted with control data for at least one of spherical lenses, cylinder lenses, prism, polarizing lenses, cross cylinder lenses and a plurality of filters by user's touch; and a data displaying page for displaying examination data received from an auto Refractometer/Keratometer and phoropter data showing status of the auto phoropter, wherein the respective pages are respectively displayed in the whole screen of the smart pad when displayed in the screen of the smart pad, and wherein the main page, the chart control page, the phoropter control page, and the data displaying page are changed among others by at least one of user's touch and button control of the smart pad.

The present invention may have the following advantages.

The present invention has an advantage in that a conventional smart pad is used in controlling ophthalmic instrument such as an auto phoropter, auto chart instrument, etc., thereby giving easy operation and control therefor.

In particular, advanced functions of the smart pad equipped with touch screen, such as finger touch (finger tapping), the number of touched finger, finger's movement such as slide motion in a state that at least one finger is touched to the screen are used in controlling ophthalmic instrument such as an auto phoropter, auto chart instrument, etc., thereby enabling control of ophthalmic instruments intuitive and easier.

In addition, an image of a phoropter is displayed in the screen of the smart pad, a plurality of control portions for controlling the auto phoropter in the image of a phoropter, and the auto phoropter is controlled by user's touch, particularly combination of finger touch and movement, thereby enabling control of ophthalmic instruments intuitive and easier.

In addition, the present invention has an advantage in that the ophthalmic instruments are controlled by receiving examination result from an auto Refractometer/Keratometer and an auto phoropter, saving the received examination data, and using the previously saved examination data in controlling the ophthalmic instruments, thereby enabling integrated management and post management for the examination result of the ophthalmic instruments.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE INVENTION

Reference will now be made in detail to the preferred embodiments of the present invention, examples of which are illustrated in the accompanying drawings.

Hereinafter, method for wireless control of ophthalmic instrument in accordance with the present invention will be explained in more detail with reference to the attached drawings.

Figure 1:
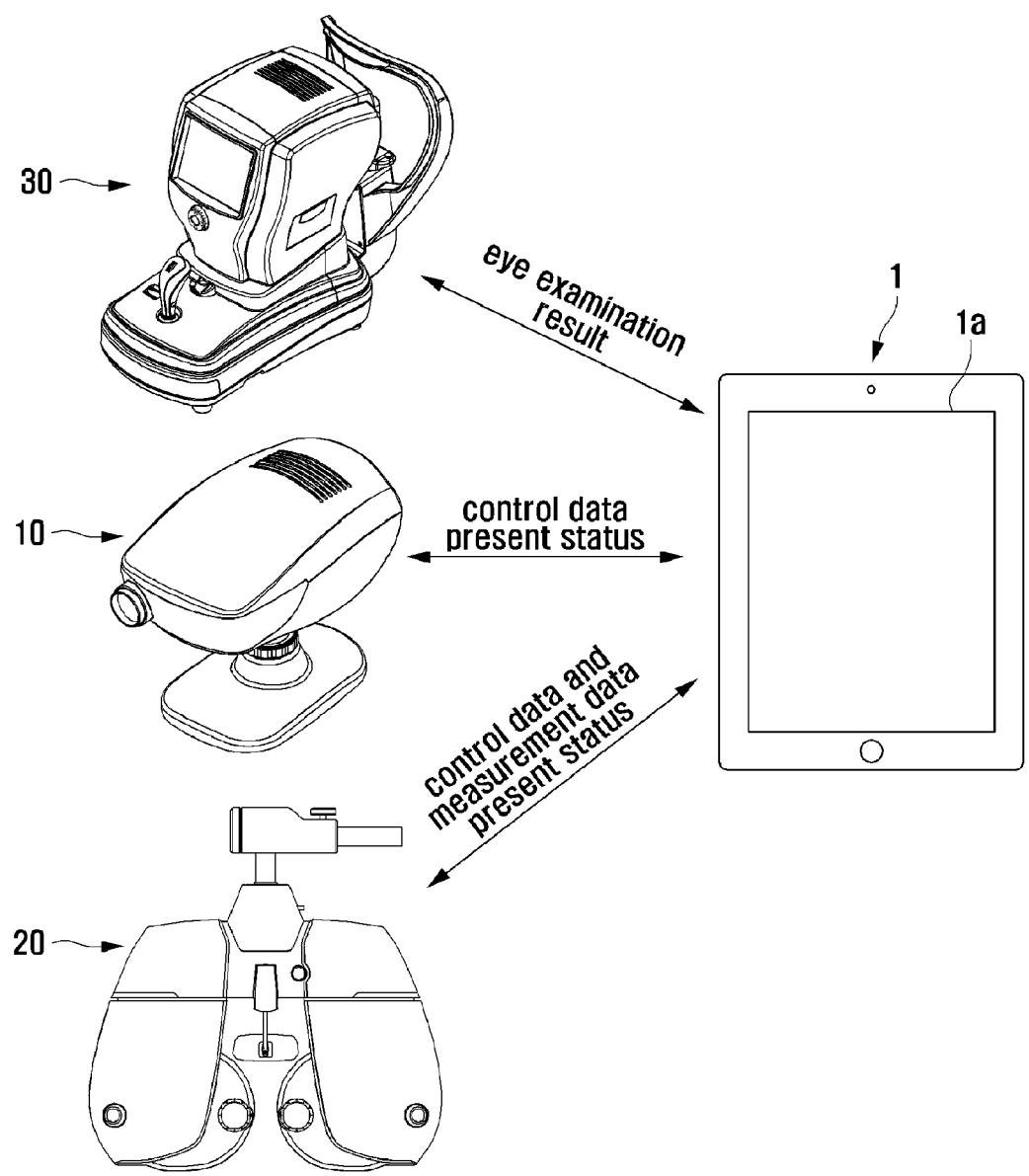
FIG. 1 is a conceptual diagram showing an ophthalmic instrument system to which the method for wireless control of ophthalmic instrument in accordance with the present invention is applied.

An ophthalmic instrument system to which the method for wireless control of ophthalmic instrument in accordance with the present invention is applied, may include at least one auto chart instrument 10, at least one auto phoropter 20, and a smart pad 1 for wireless control of at least one auto chart instrument 10 and at least one auto phoropter 20 as shown in FIG. 1.

The auto chart instrument 10 is an ophthalmic instrument for measuring eyesight by displaying chart images including letters, figures, etc., and may be a chart projector, an LCD chart, etc. which displaying chart images including letters, figures, etc. for measuring eyesight on a screen.

For example, the chart instrument 10, may include an image forming unit printed with images including letters, figures, etc., a light source for generating light, an optical unit for guiding the light passed the image forming unit from the light source to a screen on which at least one image of the image forming unit, and a body unit installed with the image forming unit, the light source and the optical unit.

The auto phoropter 20 is an ophthalmic instrument including spherical lenses, cylinder lenses, cross cylinder lenses, etc., in which some lens may be combined each other or among others, and performs eye tests such as eyesight test and color blindness test together with another ophthalmic instrument, a chart projector.

Particularly, the auto phoropter 20 may performs eye tests by being automatically controlled by wireless control of the smart pad 1.

The auto chart instrument 10 and the auto phoropter 20 may be installed with at least one wireless communication module such as Bluetooth module, WIFI module, infrared ray communication module, etc. in order to transmitting or receiving control data therebetween or with the smart pad 1.

The smart pad 1 is a wireless terminal having a screen 1a displaying various information, images, etc., and an OS such as IOS of Apple Inc., Android of Google Inc., Mobile OS of Microsoft, etc. is installed in the smart pad 1.

Particularly, the smart pad 1 may include a touch screen 1a operable with user's touch such as user's finger operation and a pen, and may include at least one wireless communication module in order to wireless control of the auto chart instrument 10 and the auto phoropter 2.

The wireless communication module may be at least one in Bluetooth module, WIFI module, infrared ray communication module, etc.

The smart pad 1 is installed with a control program, that is to say a control APP as the method for wireless control of ophthalmic instrument such as the an auto chart instrument 10 and the auto phoropter 20.

Figure 3:
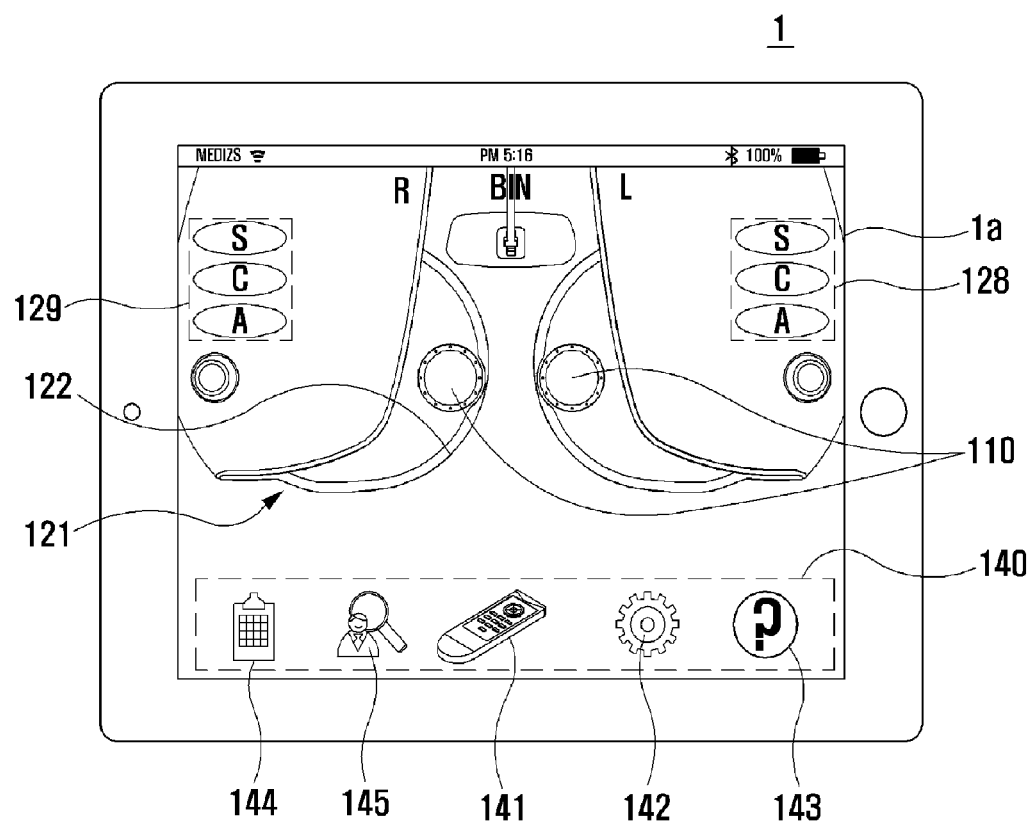
FIG. 3 is a conceptual view showing a screen of the smart pad in a state that the method for wireless control of ophthalmic instrument in accordance with the present invention is executed as an APP for the smart pad.

And as shown in FIG. 3, the control APP may be executed so that an image 121 of an ophthalmic instrument, particularly a phoropter and control data for the auto phoropter 20 may be displayed in the main page of the screen 1a of the smart pad 1.

The image 121 may be an image of an auto phoropter or a manual phoropter, and particularly may be selected in the at least one auto phoropter and at least one manual phoropter.

Herein, the image 121 of a phoropter may have a pair of circular indicating portions 110 corresponding to a pair of through hole portions of the auto phoropter 20 of a manual phoropter to which customer's eyes are positioned in order to control the auto phoropter 20 and display the controlled state of the auto phoropter 20.

In addition, the phoropter image 121, may be divided into a plurality of detailed control portions, and the plurality of detailed control portions may be used as a control portion in order to be inputted with control data for the auto chart instrument 10 and the auto phoropter 20 by user's finger operation, etc.

Particularly, since the image 121 has an image of a phoropter, at least one portion of the phoropter corresponding to at least one portion in the phoropter to be controlled, for example spherical lenses, cylinder lenses, prism etc., may be control portions for being inputted with control signals for lens rotation, PD change (width between the pair of through hole portions), optical axes of the pair of through hole portions, etc.

Concretely, as shown in FIG. 3, control portions for being inputted with control signal of PD change are respectively positioned in the portions marked as 'L ' and 'R'. And in a state that user touches the portions marked as 'L ' and 'R' by two fingers, if user decreases the width of the two fingers, control signal to make PD value decrease, and if user increases the width of the two fingers, control signal to make PD value increase in the smart pad 1.

In addition, an additional control portion 'BIN' may be marked between the portions marked as 'L' and 'R'. And in a state that user touches the control portions 'L' and 'BIN' by two fingers, if user decreases the width of the two fingers, control signal to make PD value between the center and the left side of the auto phoropter decrease, and if user increases the width of the two fingers, control signal to make PD value between the center and the left side of the auto phoropter increase in the smart pad 1.

And in a state that user touches the control portions 'BIN' and 'R' by two fingers, if user decreases the width of the two fingers, control signal to make PD value between the center and the right side of the auto phoropter decrease, and if user increases the width of the two fingers, control signal to make PD value between the center and the right side of the auto phoropter increase in the smart pad 1.

As described in the above, when the phoropter image 121 in the main page and some portions of the phoropter image 121 are used as corresponding control portions corresponding to the members of the auto phoropter to be controlled, users familiar with the structure and the functions of the phoropter may intuitively and easily control the auto phoropter.

In addition, when the phoropter image 121 is an image of a manual phoropter, users familiar with the conventional manual phoropter, may intuitively and easily control the auto phoropter 20.

The pair of circular indicating portions 110 corresponds to the pair of through hole portions of an auto phoropter or a manual phoropter through which customer looks an eye chart, especially images projected on the screen by the auto chart projector 10, and may have various shapes.

In addition, the pair of circular indicating portions 110, may show control state of the auto phoropter 20. For example, the pair of circular indicating portions 110 has red color or blue color in order to show the operation of the red and green filter, or may show control state of the special lenses such as polarizing film, prism, etc.

In addition, the pair of circular indicating portions 110 may be used as control portions for being inputted with control signals for the red and green filter, polarizing film, prism, etc.

Figure 4:
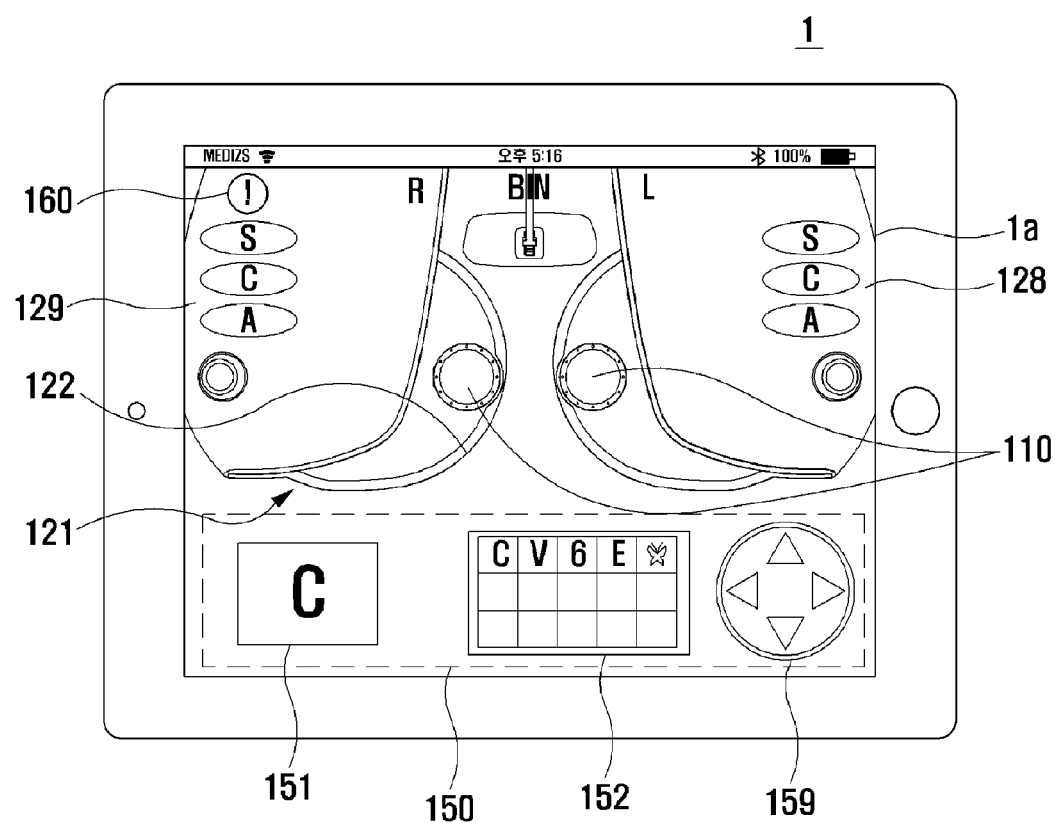
FIG. 4 is a conceptual view showing a screen of the smart pad in another state that the method for wireless control of ophthalmic instrument in accordance with the present invention is executed as an APP for the smart pad

As shown in FIGS. 3 and 4, control portions 128, 129 for being inputted with control data for controlling diopter S of spherical lens, diopter C of cylindrical lens, axis value of the auto phoropter 20 may be appropriately positioned in the main page.

And the control portions 128, 129 may display the present values for the diopter S of spherical lens, diopter C of cylindrical lens, and axis value of the auto phoropter 20.

Herein, the control portions 128, 129 and the present values for the diopter S of spherical lens, diopter C of cylindrical lens, and axis value of the auto phoropter 2, may be displayed in a predetermined time period in the main page when user touches (tapping) the phoropter image 121 by finger and/or a pen.

In addition, as another method for being inputted with control data for controlling diopter S of spherical lens, diopter C of cylindrical lens, axis value of the auto phoropter 20, the control data therefor may be inputted by tapping the screen of the smart pad 1, contact of predetermined time to the screen of the smart pad 1, or screen contact and slide motion to the screen of the smart pad 1 by user's various touch using finger and/or a pen.

Concretely, when user selects the control portions 128, 129 by contacting the control portions 128, 129, number input window, up and down indication image, etc. for being inputted with the control value may be displayed in the main page.

In addition, as still another method, when user selects the control portions 128, 129 by contacting the control portions 128, 129, dial for being inputted with the corresponding control value is displayed in the main page and the control value may be inputted by rotating and/or sliding motions of the dial by user's finger and/or a pen.

In addition, as still another method, when user selects the control portions 128, 129 by contacting the control portions 128, 129, dial for being inputted with the corresponding control value is displayed in a position corresponding to a part of outer line of the phoropter image 121 in the main page, and the control value may be inputted by rotating and/or sliding motions of the dial by user's finger and/or a pen.

In addition, as still another method, the selection of the control portions 128, 129 and input of the corresponding control value may performed by recognizing the finger number and the movement of user's finger touch when user touch the screen 1a of the smart pad 1 and corresponding the control selection of control data for at least one of spherical lenses, cylinder lenses, prism, polarizing lenses, cross cylinder lenses and a plurality of filters and being inputted with control value for at least one of spherical lenses, cylinder lenses, prism, polarizing lenses, cross cylinder lenses and a plurality of filters.

In an appropriate position in the main page, may be displayed a menu portion 140 displaying chart instrument control portion 141, setting portion 142 for wireless communication portion, user information input, customer's information input, setting instrument connection, etc., help portion 143 for APP usage, and chart portion 144 for showing eye examination data of the auto Refractometer/Keratometer 30 (first eye examination result), control state or eye examination data of the auto phoropter 20 (second eye examination result), search portion 145 for searching customer's information, etc.

When the chart control instrument portion 141 displayed in the main page, is selected by user's touch using finger and/or a pen, a chart control portion 150 displaying at least part of a plurality of images in order to be inputted with chart control data for controlling the auto chart instrument 10, may be displayed in at least a part of the main page in a state that the chart instrument control portion 141 is removed or maintained when the chart control instrument portion 141 is selected by user's touch as shown in FIG. 4.

The chart control portion 150 displays various images 152 for controlling the auto chart instrument 10 to project selected images on the projection screen or the screen of the LCD chart instrument. When some image(s) are selected by user's touch using finger and/or a pen, control signal for the auto chart instrument 10 to project the selected image(s) on the projection screen or the screen of the LCD chart instrument is generated.

The chart control portion 150 may further displays control portion for changing other images 152, chart control state displaying portion 151 displaying selected image 152 in addition to the various images 152, etc.

In addition, the chart control portion 150 may further displays control portion 159 for controlling the auto phoropter 20 besides control portion for controlling the auto chart instrument 10.

A notifying portion 160 for notifying that an additional examination result performed by the auto Refractometer/Keratometer 30 is received, may be in an appropriate position in the main page.

The notifying portion 160 is a control portion for visually notifying that that an additional examination result performed by the auto Refractometer/Keratometer 30 is received, and may generate control signal for displaying the information in the screen 1a using various method such as popup window, etc., after user's touch to the screen such as tap, screen contact of predetermined time period, screen contact and slide motion using finger and/or a pen.

The chart portion 144 is a control portion for displaying control state or eye examination data of the auto phoropter 20 (second eye examination result).

Particularly, the chart portion 144 may display control state or eye examination result of the auto phoropter 20 (second eye examination result) in the additional widow or in the main page in the screen 1a of the smart pad 1 when selected by the user's touch.

And the chart portion 144 may display the first eye examination result of the auto Refractometer/Keratometer 30 and the second eye examination result of the auto phoropter 20 in the additional widow or in the main page in the screen 1a of the smart pad 1 when selected by the user's touch.

In addition, the selection of the chart portion 144, may save the first eye examination result of the auto Refractometer/Keratometer 30 and the second eye examination result of the auto phoropter 20 in the smart pad 1, or display an order input widow for being inputted with an order such as order to transfer information to the medical information server (not shown) as an additional window or in the main page when selected by the user's touch.

When window(s) in the main page or additional page(s) is displayed in the screen 1a of the smart pad 1, window(s) in the main page or additional page(s) may be displayed by popup or slide method as usual in the computer or mobile device.

The ophthalmic instrument system in accordance with the present invention may further include at least one auto Refractometer/Keratometer 30 which measures eyesight and transfer the examination result to the smart pad 1 by wireless communication.

The auto Refractometer/Keratometer 30, is an instrument which radiates light to eyes, captures an image reflected by the retina of the eyes, analyze the captured image, and measure eyesight or eye state.

The auto Refractometer/Keratometer 30 may be installed with at least one wireless communication module such as Bluetooth module, WIFI module, infrared ray communication module, etc. in order to transmitting or receiving control data with the smart pad 1.

The ophthalmic instrument system in accordance with the present invention may a plurality of sets of the auto chart instrument 10 and the auto phoropter 20. And each set of the auto chart instrument 10 and the auto phoropter 20 of the ophthalmic instrument system may further include an auto Refractometer/Keratometer 30.

The ophthalmic instrument system in accordance with the present invention as described in the above may be controlled by the following control method.

Figure 2:
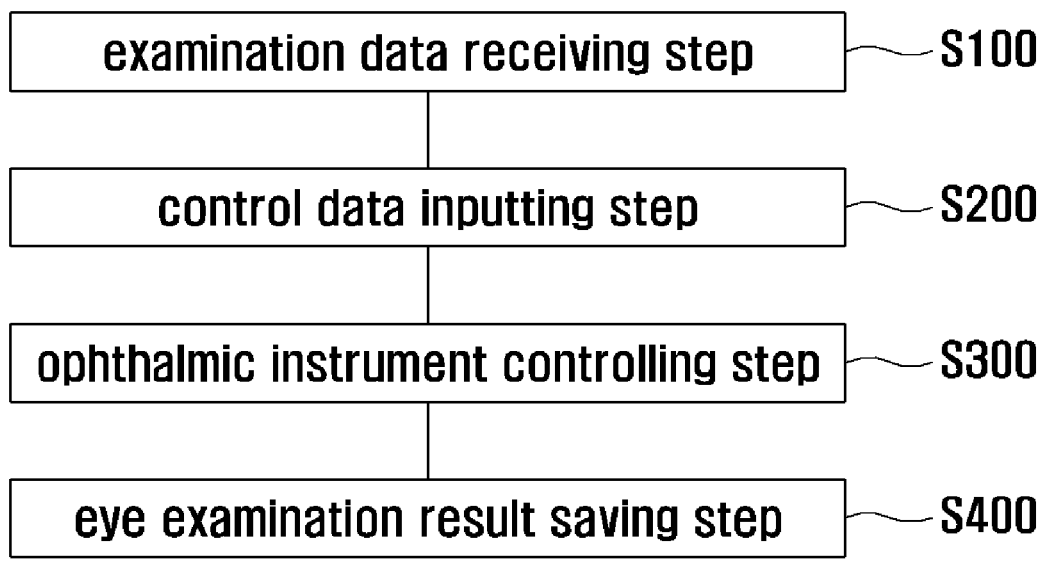
FIG. 2 is a flowchart showing the method for wireless control of ophthalmic instrument in accordance with the present invention.

As shown in FIG. 2, the method for controlling ophthalmic instrument may include control data inputting step S200 for being inputted with control data (or first eye examination result) for wireless control of one of the auto chart instrument 10 and the auto phoropter 20; and controlling step S300 for controlling one of the auto chart instrument 10 and the auto phoropter 10 according to the control data inputted during the control data inputting step S200.

The control data inputting step S200 is a step for being inputted with control data for wireless control of one of the auto chart instrument 10 and the auto phoropter 20, and in control data inputting step S200, the control data for wireless control of one of the auto chart instrument 10 and the auto phoropter 20 by displaying input tool in the main page of the screen 1a of the smart pad 1 may be inputted.

The ophthalmic instrument controlling step S300 is a step for controlling one of the auto chart instrument 10 and the auto phoropter 10 according to the control data inputted during the control data inputting step S200, and in the ophthalmic instrument controlling step S300, the smart pad 1 may control the auto chart instrument 10 and the auto phoropter 20 by generating control signal in accordance with the inputted control data by user's touch using finger or a pen on the main page displayed in the screen 1a of the smart pad 1, and transferring control signal of the control data to at least one of the auto chart instrument 10 and the auto phoropter 20 by wireless communication.

The control data inputting step S200 and the ophthalmic instrument controlling step S300 are performed in a state that the main page is displayed in the screen 1a of the smart pad 1.

And the control data inputting step S200 may include chart control portion displaying step S210 for displaying chart instrument control portion 141 in the main page, when the chart instrument control portion selected by user's touch; and chart control data receiving step S220 for displaying at least part of a plurality of images in order to be inputted with chart control data for controlling the auto chart instrument 10 in a state that the chart instrument control portion 141 is removed or maintained when the chart instrument control portion 141 is selected by user's touch.

And the control data inputting step S220 may include selected image displaying step S230 for displaying the chart control data inputted in the chart control data receiving step S220 after the chart control data receiving step S220.

Meanwhile, the control data inputting step S200 may include phoropter control portion displaying step S240 for displaying phoropter control portion in the main page in order to be inputted with control data for at least one of spherical lenses, cylinder lenses, prism, polarizing lenses, cross cylinder lenses, a plurality of filters, etc. by user's touch; and control data displaying step S250 for being inputted with control data for at least one of spherical lenses, cylinder lenses, prism, polarizing lenses, cross cylinder lenses, a plurality of filters, etc. by user's touch and displaying the control data in the main page.

After the control data displaying step S250, the finger number and the finger movement of user's finger touch to the screen 1a of the smart pad 1 are recognized and control data for at least one of spherical lenses, cylinder lenses, prism, polarizing lenses, cross cylinder lenses, a plurality of filters, etc. is inputted by the finger number and the movement of user's finger touch.

Meanwhile, the smart pad 1 may be saved with a main page, a chart control page, a phoropter control page, a data displaying page, etc., and may selectively display each page.

The main page is for displaying an image of a phoropter and control data for the auto phoropter 20.

The chart control page is for displaying at least part of a plurality of images for controlling the auto chart instrument 10 in order to be inputted with control data for the auto chart instrument 10 by user's touch.

The phoropter control page is for displaying at least one control portion in the image of a phoropter corresponding to a member of the auto phoropter 20 to be controlled, the member being one of spherical lenses, cylinder lenses, prism, polarizing lenses, cross cylinder lenses, a plurality of filters, etc. in order to be inputted with control data for at least one of spherical lenses, cylinder lenses, prism, polarizing lenses, cross cylinder lenses, a plurality of filters, etc. by user's touch.

The data displaying page is for displaying examination data received from the auto Refractometer/Keratometer 30 and phoropter data showing status of the auto phoropter 20 in the examination data receiving step S100.

Herein the respective pages are respectively displayed in the whole screen 1a of the smart pad 1 when displayed in the screen 1a of the smart pad 1.

And the main page, the chart control page, the phoropter control page, and the data displaying page are changed among others by at least one of user's touch using finger and/or a pen, and button control of the smart pad 1.

The control data is inputted by at least one of user's finger operation and a pen in the control data inputting step S200.

The finger number and the finger movement of user's finger touch to the screen 1a of the smart pad 1 are recognized and the control data is inputted by the finger number and the movement of user's finger touch in the control data inputting step S200.

The method for controlling the ophthalmic instrument may further include examination data receiving step S100 for receiving examination data (first eye examination data) from the auto Refractometer/Keratometer 30 by wireless communication in order to refer examination data from the auto Refractometer/Keratometer 30 in controlling the auto phoropter 20. Herein the received examination data may be displayed in the screen 1a of the smart pad 1.

The examination data receiving step S100 is for receiving examination data (first eye examination data) from the auto Refractometer/Keratometer 30 by wireless communication. In the examination data receiving step S100, the received examination data may be displayed in the screen 1a of the smart pad 1. In addition, in the examination data receiving step S100, the received examination data may be saved in the smart pad 1 or the save server (not shown) by wireless communication.

Meanwhile, the examination data received from the auto Refractometer/Keratometer 30 in the examination data receiving step S100 may be referred to for being inputted with the control data for wireless control of at least one of the auto chart instrument 10 and the auto phoropter 20 in the control data inputting step S200.

The control data inputting step S200 may control the auto phoropter 20 by wireless communication by reflecting the received examination data in the examination data receiving step S100 before the control data is inputted for the auto phoropter 20.

Meanwhile, the method for controlling ophthalmic instrument may further include eye examination result saving step S400 for saving the eye examination data of the auto Refractometer/Keratometer 30 (first eye examination result) and the examination data examined by the auto phoropter 20 (second eye examination result) in the ophthalmic instrument controlling step S300 as eye examination result in the smart pad 1 and/or server for saving eye examination result after the ophthalmic instrument controlling step S300.

Herein customer's information such as name, address, sex, age, photo, etc., examination date, user's information, reference information, etc. may be saved in addition to the eye examination data in the eye examination result saving step S400.

The eye examination data may be saved as an electronic document having a format which can be saved in the medical information server for saving medical information in the eye examination result saving step S400. And the eye examination data may be saved in the standard electronic document which can be received to official medical information server the according the user's selection.

In connection with the saving or the transformation to the standard electronic document, the APP for the method for wireless control of ophthalmic instrument installed in the smart pad 1 may be updated or upgraded by wireless communication with the update or upgrade server in order to save or transform the eye examination data to the standard electronic document which has a format required by the official medical information server.

The eye examination result saving step S400 is for saving the eye examination data of the auto Refractometer/Keratometer 30 (first eye examination result) and the examination data examined by the auto phoropter 20 (second eye examination result) in the ophthalmic instrument controlling step S300 as eye examination result in the smart pad 1 and/or server for saving eye examination result after the ophthalmic instrument controlling step S300.

Figure 5:
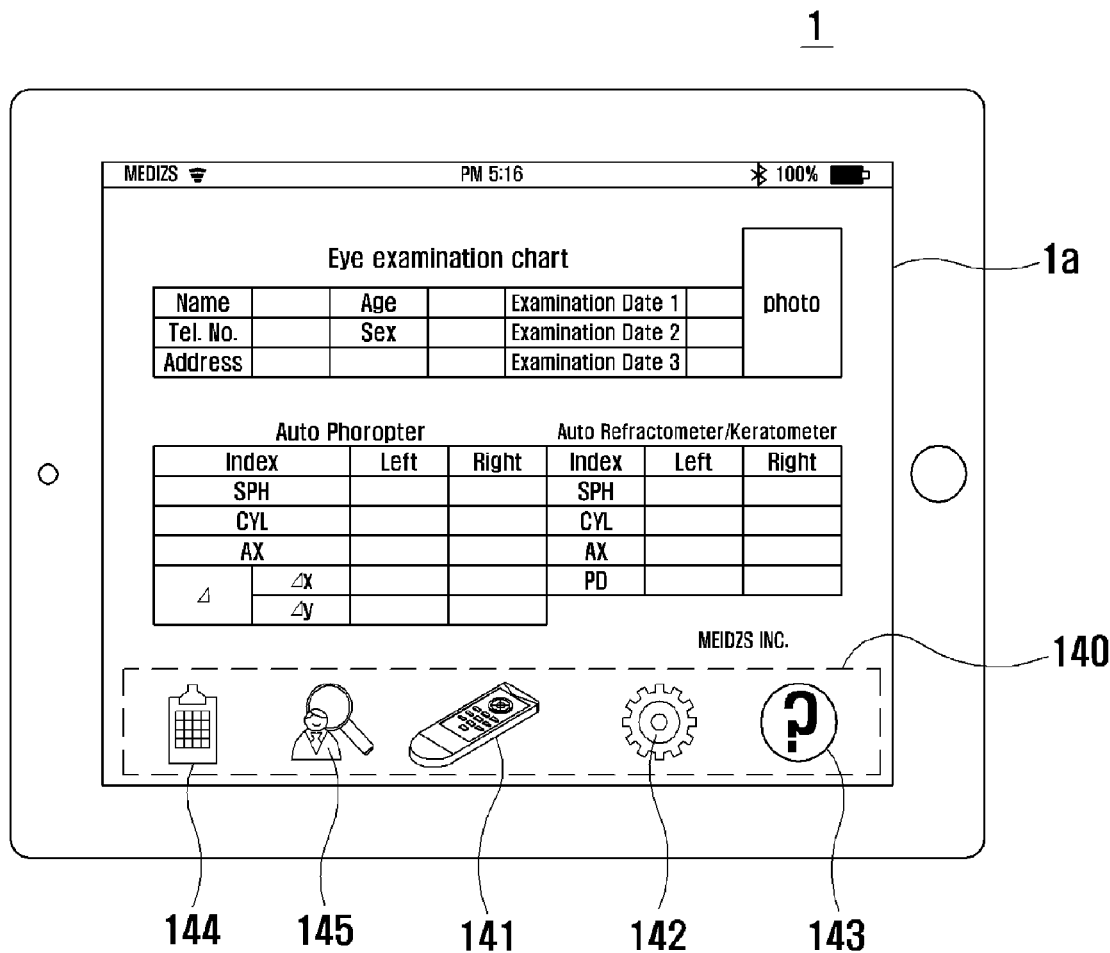
FIG. 5 is a conceptual view showing a screen of the smart pad in which examination result measured by the ophthalmic instrument system of FIG. 1 is displayed as an eye examination chart.

Meanwhile, the eye examination data of the auto Refractometer/Keratometer 30 (first eye examination result) and the examination data examined by the auto phoropter 20 (second eye examination result) in the ophthalmic instrument controlling step S300 may be displayed in the screen 1a of the smart pad 1 in accordance with the selection of the chart portion 144 as shown in FIG. 5.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A method for wireless control of an auto chart instrument and an auto phoropter by using a smart pad, comprising:
   control data inputting step for being inputted with control data for wireless control of one of the auto chart instrument and the auto phoropter; and
   controlling step for controlling one of the auto chart instrument and the auto phoropter according to the control data inputted during the control data inputting step.

2. The method according to claim 1, wherein in the control data inputting step and the ophthalmic instrument controlling step, an image of a phoropter and control data for the auto phoropter are displayed in a screen of the smart pad.

3. The method according to claim 2, wherein a portion of the image of a phoropter corresponding to a member of the auto phoropter to be controlled is used as a control portion in the control data inputting step and the ophthalmic instrument controlling step.

4. The method according to claim 2, wherein the control data inputting step comprises:
   chart control portion displaying step for displaying chart instrument control portion in the main page, when the chart instrument control portion selected by user's touch; and
   chart control data receiving step for displaying at least part of a plurality of images in order to be inputted with chart control data for controlling the auto chart instrument in a state that the chart instrument control portion is removed or maintained when the chart instrument control portion is selected by user's touch.

5. The method according to claim 4, wherein the control data inputting step comprises selected image displaying step for displaying the chart control data inputted in the chart control data receiving step after the chart control data receiving step.

6. The method according to claim 1, wherein the control data inputting step comprises:
   phoropter control portion displaying step for displaying phoropter control portion in a main page in order to be inputted with control data for at least one of spherical lenses, cylinder lenses, prism, polarizing lenses, cross cylinder lenses and a plurality of filters by user's touch; and
   control data displaying step for being inputted with control data for at least one of spherical lenses, cylinder lenses, prism, polarizing lenses, cross cylinder lenses and a plurality of filters by user's touch and displaying the control data in the main page.

7. The method according to claim 6, wherein after the control data displaying step, the finger number and the finger movement of user's finger touch to the screen of the smart pad are recognized and control data for at least one of spherical lenses, cylinder lenses, prism, polarizing lenses, cross cylinder lenses and a plurality of filters is inputted by the finger number and the movement of user's finger touch.

8. The method according to claim 1, wherein the control data is inputted by at least one of user's finger operation and a pen in the control data inputting step.

9. The method according to claim 8, wherein the finger number and the finger movement of user's finger touch to the screen of the smart pad are recognized and the control data is inputted by the finger number and the movement of user's finger touch in the control data inputting step.

10. The method according to claim 1, further comprising:
    examination data receiving step for receiving examination data from an auto refractometer/keratometer by wireless communication.

11. The method according to claim 10, wherein the examination data received from an auto refractometer/keratometer in the examination data receiving step are used for being inputted with the control data for wireless control of at least one of the auto chart instrument and the auto phoropter in the control data inputting step.

12. The method according to claim 1, wherein the smart pad is saved with:
    a main page for displaying an image of a phoropter and control data for the auto phoropter;
    a chart control page for displaying at least part of a plurality of images for controlling the auto chart instrument in order to be inputted with control data for the auto chart instrument by user's touch;
    a phoropter control page for displaying at least one control portion in the image of a phoropter corresponding to a member of the auto phoropter to be controlled, the member being one of spherical lenses, cylinder lenses, prism, polarizing lenses, cross cylinder lenses and a plurality of filters in order to be inputted with control data for at least one of spherical lenses, cylinder lenses, prism, polarizing lenses, cross cylinder lenses and a plurality of filters by user's touch; and
    a data displaying page for displaying examination data received from an auto refractometer/keratometer and phoropter data showing status of the auto phoropter,
    wherein the respective pages are respectively displayed in the whole screen of the smart pad when displayed in the screen of the smart pad, and
    wherein the main page, the chart control page, the phoropter control page, and the data displaying page are changed among others by at least one of user's touch and button control of the smart pad.

13. A method for wireless control of an auto chart instrument and an auto phoropter by using a smart pad, comprising:
    control data inputting step for being inputted with control data for wireless control of one of the auto chart instrument and the auto phoropter; and
    controlling step for controlling one of the auto chart instrument and the auto phoropter according to the control data inputted during the control data inputting step,
    wherein the smart pad is saved with:
    a main page for displaying an image of a phoropter and control data for the auto phoropter;

a chart control page for displaying at least part of a plurality of images for controlling the auto chart instrument in order to be inputted with control data for the auto chart instrument by user's touch;

a phoropter control page for displaying at least one control portion in the image of a phoropter corresponding to a member of the auto phoropter to be controlled, the member being one of spherical lenses, cylinder lenses, prism, polarizing lenses, cross cylinder lenses and a plurality of filters in order to be inputted with control data for at least one of spherical lenses, cylinder lenses, prism, polarizing lenses, cross cylinder lenses and a plurality of filters by user's touch; and a data displaying page for displaying examination data received from an auto refractometer/keratometer and phoropter data showing status of the auto phoropter, wherein the respective pages are respectively displayed in the whole screen of the smart pad when displayed in the screen of the smart pad, and wherein the main page, the chart control page, the phoropter control page, and the data displaying page are changed among others by at least one of user's touch and button control of the smart pad.

14. The method according to claim 13, wherein in the control data inputting step and the ophthalmic instrument controlling step, an image of a phoropter and control data for the auto phoropter are displayed in a screen of the smart pad.

15. The method according to claim 14, wherein a portion of the image of a phoropter corresponding to a member of the auto phoropter to be controlled is used as a control portion in the control data inputting step and the ophthalmic instrument controlling step.

16. The method according to claim 14, wherein the control data inputting step comprises:

chart control portion displaying step for displaying chart instrument control portion in the main page, when the chart instrument control portion selected by user's touch; and chart control data receiving step for displaying at least part of a plurality of images in order to be inputted with chart control data for controlling the auto chart instrument in a state that the chart instrument control portion is removed or maintained when the chart instrument control portion is selected by user's touch.

17. The method according to claim 16, wherein the control data inputting step comprises selected image displaying step for displaying the chart control data inputted in the chart control data receiving step after the chart control data receiving step.

18. The method according to claim 13, wherein the control data inputting step comprises:

phoropter control portion displaying step for displaying phoropter control portion in a main page in order to be inputted with control data for at least one of spherical lenses, cylinder lenses, prism, polarizing lenses, cross cylinder lenses and a plurality of filters by user's touch; and control data displaying step for being inputted with control data for at least one of spherical lenses, cylinder lenses, prism, polarizing lenses, cross cylinder lenses and a plurality of filters by user's touch and displaying the control data in the main page.

19. The method according to claim 18, wherein after the control data displaying step, the finger number and the finger movement of user's finger touch to the screen of the smart pad are recognized and control data for at least one of spherical lenses, cylinder lenses, prism, polarizing lenses, cross cylinder lenses and a plurality of filters is inputted by the finger number and the movement of user's finger touch.

20. The method according to claim 13, wherein the control data is inputted by at least one of user's finger operation and a pen in the control data inputting step.

* * * * *